(12) United States Patent
Grit et al.

(10) Patent No.: US 7,896,930 B2
(45) Date of Patent: Mar. 1, 2011

(54) PROCESS FOR PREPARING BLEACHING/HIGHLIGHTING COMPOSITION AND USE OF SUCH COMPOSITIONS

(75) Inventors: Mustafa Grit, Gernsheim (DE); Heiko Maile, Frankfurt (DE)

(73) Assignee: KPSS-Kao Professional Salon Services GmbH, Darstadt (DE)

( * ) Notice: Subject to any disclaimer, the term of this patent is extended or adjusted under 35 U.S.C. 154(b) by 30 days.

(21) Appl. No.: 12/274,798

(22) Filed: Nov. 20, 2008

(65) Prior Publication Data

US 2009/0133199 A1 May 28, 2009

(51) Int. Cl.
*D06P 3/04* (2006.01)
*A61K 8/00* (2006.01)
*A61K 8/41* (2006.01)
*A61K 8/30* (2006.01)
*A61Q 5/10* (2006.01)
*C11D 3/00* (2006.01)
*C11D 7/54* (2006.01)
*C11D 7/18* (2006.01)
*C11D 9/42* (2006.01)

(52) U.S. Cl. .................. 8/405; 8/404; 8/407; 8/431; 510/367

(58) Field of Classification Search .................. 8/405, 8/404, 407, 431; 510/367
See application file for complete search history.

(56) References Cited

U.S. PATENT DOCUMENTS

| 4,975,295 | A |   | 12/1990 | Sierra |        |
|-----------|---|---|---------|--------|--------|
| 5,891,423 | A | * | 4/1999  | Weeks  | 424/62 |

FOREIGN PATENT DOCUMENTS

| EP | 0778020 A    | 6/1997  |
|----|--------------|---------|
| EP | 1803436 A    | 7/2007  |
| WO | 2004/105728 A| 12/2004 |

OTHER PUBLICATIONS

English Language Abstract For EP 0778020A, Jun. 11, 1997.

* cited by examiner

*Primary Examiner*—Lorna M Douyon
*Assistant Examiner*—Tanisha Diggs
(74) *Attorney, Agent, or Firm*—Norris McLaughlin & Marcus, PA

(57) ABSTRACT

The present invention relates to a process for bleaching hair wherein a water free bleaching composition, preferably in form of a dust free powder or a granulate comprising at least one compound with bleaching and/or highlighting effect is mixed with an liquid oxidizing composition wherein water free bleaching powder is passed through a sieve.

6 Claims, No Drawings

PROCESS FOR PREPARING BLEACHING/HIGHLIGHTING COMPOSITION AND USE OF SUCH COMPOSITIONS

The present invention relates to a process for bleaching hair wherein a water free bleaching composition, preferably in form of a dust free powder or a granulate comprising at least one compound with bleaching and/or highlighting effect is mixed with an liquid oxidizing composition wherein water free bleaching powder is passed through a sieve.

Hair bleaching is a common practice for ages. It is based on oxidative decomposition of hair colour, which is usually done using peroxide or peroxide releasing compounds such as persulfates. Due to highly irritating potential of these bleaching ingredients and dustiness of powder compositions, it is preferred to provide granular composition where dust is reduced by agglomerating small particles into granulates using various binding agents. Most popular binding agent is mineral oil, which was the subject matter of EP 560 088 B1. Furthermore, EP 778 020 A1 suggests the use of oil and wax compounds or their mixtures for preparation of suspensions.

The bleaching of human hair customarily consists of a process with the following steps: Homogenous mixing of a water-free preparation, preferably a powder, comprising at least one compound with a bleaching or brightening effect, in particular a solid peroxide salt, preferably ammonium, potassium and/or sodium persulfate or earth alkali peroxide, with an aqueous hydrogen peroxide composition, application of this composition onto the hair, and rinsing after bleaching is completed. It has been known for some time that use of these components is effective with regard to the bleaching, but higher concentrations can lead to hair damage and/or scalp irritation. In practice it has further been observed that inhomogeneous mixing of the bleaching powder composition with the liquid composition comprising at least one oxidizing agent results not only in inhomogeneous highlighting and/or bleaching but also scalp irritation potential increases considerably.

Inhomogeneous mixing possibly occurs due to the formation of agglomerates during storage and/or during preparation of dust free powders and/or granulates. As mentioned above, for granulation and/or dust reduction hydrophobic ingredients are usually used.

It is also noted that inhomogeneous mixing may also be caused in case such a process is carried out by a person who does not have the required proper qualification and/or in case that necessary attention is not paid during the mixing process.

The inventors of the present invention aimed at providing solution to the inhomogeneous mixing of powder bleaching composition into liquid oxidizing composition It has surprisingly been found out that in case that water free powder and/or granular bleaching composition is passed through a sieve during addition of the said powder into the liquid oxidizing composition, more homogeneous bleaching is achieved and more importantly side effects such as scalp irritation potential is considerably reduced, if not totally removed.

Accordingly first object of the present invention is process for preparing bleaching and/or highlighting composition wherein a water free bleaching powder and/or granules is mixed with a liquid composition, comprising preferably at least one oxidizing agent wherein powder composition is added to a liquid composition by passing through a sieve.

Second object of the present invention is that process for preparing bleaching and/or highlighting composition wherein a water free bleaching composition is mixed with a cosmetic liquid composition and the resulting mixture is mixed with a second liquid composition comprising at least one oxidizing agent wherein powder composition is added to a cosmetic liquid composition by passing through a sieve.

Third object of the present invention is that process for preparing bleaching and/or highlighting composition wherein a water free bleaching composition is mixed with a cosmetic liquid composition comprising at least one direct dye and the resulting mixture is mixed with a second liquid composition comprising at least one oxidizing agent wherein powder composition is added to a cosmetic liquid composition by passing through a sieve.

The forth object of the present invention is that process for preparing bleaching and/or highlighting and colouring composition wherein a water free bleaching composition is mixed first with a powder composition comprising at least one direct dye and the resulting mixture is mixed with a cosmetic liquid composition comprising at least one oxidizing agent wherein said powder composition mixture is added to a cosmetic liquid composition comprising at least one oxidizing agent by passing through a sieve.

The fifth object of the present invention is that process for preparing bleaching and/or highlighting and colouring composition wherein a water free bleaching composition is mixed first with a powder composition comprising at least one direct dye and the resulting mixture is mixed with a cosmetic liquid composition, and further the resulting mixture is mixed with a liquid composition comprising at least one oxidizing agent wherein said powder composition mixture is added to a cosmetic liquid composition by passing through a sieve.

Further object of the present invention is the use of composition prepared according to any of the above mentioned processes for bleaching and/or highlighting and/or colouring hair.

In the present invention all powder compositions, either one already available or resulted in mixing immediately prior to use of the two powder compositions, are added to the liquid composition by passing through a sieve.

Powder compositions comprise particles of variable sizes. It is important within the meaning of the present invention that all of the powder put onto the sieve is passed through the sieve. In order to realize this relatively small opening size of the sieve is required. It has been found out that opening size of sieve is 5 mm and smaller, preferably 3 mm and smaller, more preferably 1 mm and smaller and most preferred 0.5 mm and smaller.

It should be noted that the sieve opening size should be selected according to the particle size distribution of the powder mixture. In the course of testing it was observed that for non granulated powder compositions 0.5 mm opening size is fully satisfactory. On the other hand, for granulated powders, a larger sieve opening size such as 1 mm is suitable which at the same time prevents dusting during sieving.

Selection of the sieve material can play an important role in order to minimize any contamination into the bleaching composition. Therefore, sieve material should be selected carefully from the materials which do not interact with the powder water free bleaching compositions.

Bleaching and or highlighting composition within the meaning of the present invention is water free powder or granular or dust free compositions. With the term water free it is meant that no additional water or any aqueous composition is added to the composition. However, it should be understood that the raw materials used may comprise water at low concentrations and therefore, from the experience, up to 1% water content does not have any influence on the stability and incorporated into compositions of the present invention in the form of bound water of individual chemicals.

According to the present invention, the water free powder composition comprises at least one compound with bleaching and/or highlighting effect. Suitable compounds are in general peroxides. Useful as such are in particular persulfates such as sodium and potassium persulfate, ammonium persulfate, earth alkali peroxides such as magnesium peroxide, melamine peroxide or urea peroxide or phtholimidoperoxyhexanoic acid. The proportion of peroxides is at least 5%, preferably in the range of 10 to 80%, more preferably 20 to 60% by weight, calculated to total composition prior to mixing with oxidizing lotion.

According to the invention, the water free composition can also comprise 0.1% to 10% by weight, calculated to total composition prior to mixing with oxidizing lotion, at least one ammonium salts. Suitable ammonium salts are ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate and ammonium lactate. Compositions may also comprise mixture or ammonium salts.

Preferred thereof are the ammonium phosphates, such as $NH_4H_2PO_4$, $(NH_4)_2HPO_4$, $(NH_4)_2NaPO_4$, $NaNH_4HPO_4$ or $NH_4Na_2PO_4$, ammonium chloride, ammonium sulfate and diammonium hydrogen citrate, as well as ammonium chloride, preferably in an amount from 0.1% to 10% by weight, calculated to total composition prior to mixing with oxidizing lotion.

As known from EP 609 796 A2, the ammonium compounds can also be used as sole bleaching agent in respectively higher amounts.

The total proportion of the compounds with bleaching and/or highlighting effect preferably ranges from 5% to 85%, preferably 10% to 80%, more preferably 20 to 70% and most preferably 30 to 60% by weight calculated to total composition prior to mixing with oxidizing lotion.

In addition to the active component, compositions also comprise the components customarily used in such compositions: In particular inert pulverulent carrier materials, these are for example, pyrogenic silicium dioxide, starch powder, etc., alkalizing agents, such as sodium metasilicate, surface-active substances, binding agents, etc. In order to avoid repetition, reference is made to the respective standard literature, for example, K. Schrader and A. Domsch, "Cosmetology—Theory and Practice (2005, Verlag für Chemische Industrie), pages 142 to 151.

Composition of the present invention may further comprise lipophilic ingredients such as vegetable oils, for example, jojoba oil or any other; petrolatum liquid paraffins, especially paraffinum perliquidum and parafiinum subliquidum; silicone oils; hydropobic fatty acid esters such as octyl palmitate, isocetyl palmitate, isopropyl palmitate and octyl stearate, $C_{10}$- to $C_{36}$-fatty acid triglycerides, as well as their mixtures. In the case that the use is wished among those the most preferred ones are silicone oils, jojoba oil, fatty acid esters, paraffin oils, combinations of fatty acid esters and paraffin oils. Fatty acid esters and/or paraffin oils and/or silicone oils are particularly preferred. Concentration of these lipophilic compounds are used in a total amount of about 0.1 to 20 percent by weight, preferably from 1 to 15 percent by weight, and more preferably from 2 to 10 percent by weight, calculated to total composition prior to mixing with oxidizing lotion.

Further, in another preferred form of the invention water free composition for bleaching and/or highlighting hair comprises polymers from the group consisting of cellulose polymer compounds, alginate, polysaccharides and acrylic acid polymers, preferably methyl cellulose compounds, ethyl cellulose compounds, hydroxyethylcellulose compounds, methylhydroxyethylcellulose compounds, methylhydroxypropylcellulose compounds, carboxymethyl cellulose compounds, alginic acids, sodium alginates, ammonium alginates, calcium alginates, gum arabic, guar gum or xanthan gum, or acrylic acid polymers with molecular weights from about 1,250,000 to 4,000,000, alone or in combination with each other. The polymers are used in a total amount of 0.1 to 15%, preferably from 0.2 to 10%, and more preferably in an amount of from 0.5 to 7.5% by weight, calculated to total composition prior to mixing with oxidizing lotion.

Bleaching and/or highlighting composition can also comprise cationic polymers as conditioning and/or thickening agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 4, Polyquaternium 6, Polyquaternium 7, Polyquaternium 10, Polyquaternium 11, Polyquaternium 16, Polyquaternium 22, Polyquaternium 24, Polyquaternium 28, Polyquaternium 30, Polyquaternium 37, Polyquaternium 36, Polyquaternium 46, Polyquaternium 67, and Polyquaternium 72.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

Typical concentration range for any of the cationic conditioners mentioned above can be 0.1-7.5% by weight, preferably 0.3-5% by weight and more preferably 0.5-2.5% by weight, calculated to total composition prior to mixing with an oxidizing agent.

Water free bleaching composition of the present invention may comprise further dialkyl carbonate of general formula $$R_1OC(O)OR_2$$

where $R_1$ and $R_2$ are independent from each other linear or branched saturated alkyl chains with 6 to 22 C atoms. Preferred dialkyl carbonate is selected from di(caprylyl) carbonate and di(ethylhexyl) carbonate. Concentration of dialkyl carbonate may vary between 0.1 and 30% by weight calculated to total composition.

Within the meaning of the present invention bleaching and/or highlighting compositions does not have to be a dust free composition; however this is preferred as the dust spread around during dosing and/or sieving may cause unwanted reactions.

The average particle size of the dust free bleaching powder composition according to the invention is generally range below 1 mm, preferably below 500 µm, more preferably less than 400 µm and in particular about 25 to about 100 µm, thus ensuring excellent processing capability, i.e. miscibility with an aqueous hydrogen peroxide solution prior to application onto human hair.

The dust free powder composition can be produced with processes such as by mixing the powdery ingredients first and subsequently adding lipophilic ingredient(s) and by fluidized bed method. In fluidized bed method, powder ingredients are mixed in a vessel and made flowing by inletting an air flow which may be heated (preferred when using waxy component) or carried out at room (ambient) temperature and while the powder mix freely "flowing" lipophilic ingredient and/or mixture with any other liquid component is sprayed from a nozzle mounted above the powder batch.

The bleaching and/or brightening composition of the present invention is mixed prior to application with an oxidizing lotion comprising at least one oxidizing agent. The oxidizing agents suitable are hydrogen peroxide, urea peroxide, melamin peroxide or perborate salts. The most preferred is hydrogen peroxide. Such composition comprises 2 to 12% by weight at least one oxidizing agent preferably hydrogen peroxide and is either a solution or in the form of an emulsion. The mixing ratio is very much dependent on the level of bleaching effect aimed, i.e. the level of highlighting and/or bleaching and darkness of hair before bleaching, and can be adjusted accordingly by hair dressers. However, generally mixing ratio is within the range of 0.5 to 4 by weight (bleaching composition to oxidizing composition), preferably in the range of 1 to 2.5 by weight.

The pH of the ready to use product, mixture of water free bleaching powder and oxidizing lotion, is in the range of 8 to 11.5, in particular between 9 and 11.

Water free bleaching powder composition can also be mixed with any other aqueous cosmetic composition prior to mixing with a composition comprising at least one oxidizing agent. Cosmetic composition mixed with powder bleaching composition comprises preferably at least one alkalizing agent such as alkanolamines such as monoethanolamine, triethanolamine and ammonia to achieve alkaline conditions especially in the pH range of 8 to 11.5, in particular between 9 and 11.

The cosmetic composition mentioned above can further comprise direct dyes. In principal any direct dye is suitable, however, the preferred ones are cationic and nitro dyes and their mixtures. The most preferred are cationic direct dyes.

Suitable anionic direct dyes in dyeing composition are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27 and DC Yellow 10.

Suitable cationic dyes in dyeing composition are in principal those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87 and Basic Orange 33. The most preferred ones are Basic red 51, Basic Yellow 87 and Basic Orange 33 sold by CIBA.

Additionally, the dyeing compositions of the present invention may comprise neutral dyes (HC dyes), so called nitro dyes for shading purposes. Some examples to those are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

According to the invention, the aqueous cosmetic composition comprises one or more direct dye at a concentration of 0.1 to 7.5% by weight calculated to the total composition prior to mixing with bleaching and oxidizing compositions mentioned above.

Powder bleaching compositions can also be mixed first with another powder composition which comprises at least one direct dye. In principal for such composition any direct dye mentioned above is suitable, however the preferred ones are cationic and nitro dyes and their mixtures. Most preferred ones are cationic direct dyes.

The above mentioned direct dyes of cationic, anionic and nonionic character can also be added into the water free bleaching and/or highlighting composition at the concentration given in the above paragraph. The direct dyes of different characters can certainly be mixed as well.

Any aqueous composition mentioned above can comprise one or more of the following ingredients disclosed below.

Aqueous compositions according to the present invention can be in the form of emulsion, solution, dispersion and/or gel. Emulsion is the preferred form.

In the case that the aqueous composition is in the form of an emulsion, it comprises as an emulsion base at least one fatty alcohol or mixture of fatty alcohols with the chain length of 14 to 22 C atoms. Examples to suitable fatty alcohols, without limiting the choice, are myristyl alcohol, cetyl alcohol, stearyl alcohol, behenyl alcohol and cetostearyl alcohol. The most preferred is cetostearyl alcohol well known with its trade name Lanette O or as Lanette N in mixture with sodium cetearyl sulfate from Cognis.

The concentration of fatty alcohol(s) is in the range from 0.5 to 20%, preferably 1 to 15% by weight, calculated to total composition prior to mixing with oxidizing and bleaching and/or highlighting composition.

Aqueous compositions according to present invention comprises surfactants selected from anionic, nonionic, amphoteric (or zwiterionic) and/or cationic surfactants as emulsifier or solubilizer. Cationic surfactants are as well used as hair conditioners in the dyeing composition.

Anionic surfactants suitable within the scope of the invention are in principal known from the cleansing compositions These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof as well as alkyl amido polyether carboxylic acids and salts thereof. Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants.

An overview of the anionic surfactants suitable for the present invention can furthermore be found in the monography of K. Schrader, "Grundlagen und Rezepturen der Kosmetika", $2^{nd}$ Ed. (1989, Hüthig Buchverlag), pp. 595-600 and pp. 683 to 691.

Further surfactants in the aqueous compositions according to the invention are nonionic surfactants alone or in admixture with anionic surfactants. These are described as well in Schrader, I.c., on pages 600-601 and pp. 694-695. Especially suited nonionic surfactants are, for example, long-chain fatty acid mono- and dialkanolamides, such as coco fatty acid mono- or diethanolamide and myristic fatty acid mono or diethanolamide, stearic acid mono or diethanolamide. Further nonionic surfactants suited are alkyl polyglucosides with an alkyl group of 8 to 18 carbon atoms, and with 1 to 5 glucoside units. Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name PLURONICS®, as well as fatty alcohol ethoxylates. Further nonionic surfactants preferred in the aqueous compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 25, preferably about 10 and about 20.

As further surfactant component, aqueous compositions according to the invention can also contain amphoteric or zwitterionic surfactants. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Aqueous composition can contain cationic surfactants as emulsifier, solubilizer and/or conditioning ingredients according to the formula, but not limited to.

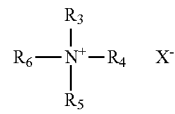

where $R_3$ is a saturated or unsaturated, branched or linear alkyl chain with 8-22 C atoms or

where $R_7$ is saturated or unsaturated, branched or linear alkyl chain with 7-21 C atoms and n has typical value of 1-4 or

where $R_8$ is saturated or unsaturated, branched or linear alkyl chain with 7-21 C atoms and n has typical value of 1-4, and $R_4$ is H or unsaturated or saturated, branched or linear alkyl chain with 1-22 C atoms or

or

where $R_7$, $R_8$ and n are same as above.

$R_5$ and $R_6$ are H or lower alkyl chain with 1 to 4 Carbon atoms, and X is typically chloride, bromide, methosulfate.

Typical examples of those ingredients are cetyl trimethly ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Concentration of one or more surfactants in aqueous composition is in the range of 0.1 to 10%, preferably 0.2 to 7.5% and most preferably 0.2-5% by weight, calculated to the total dyeing composition.

Aqueous composition and water free bleaching composition of the present invention preferably comprise an organopolysiloxane wherein at least one silicium atom is linked to an alkylene group having a hetero-atom, in particular a nitrogen atom, with a poly-(N-acyl alkyleneimine) units of the formula

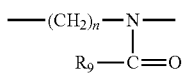

wherein n is a number from 1 to 5 and $R_9$ is hydrogen, a $C_1$-$C_{12}$-alkyl or cycloalkyl, aralkyl or aryl group. Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

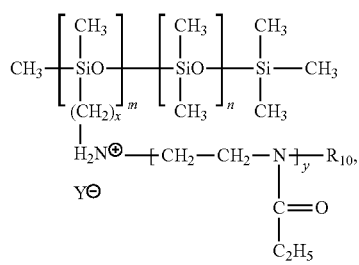

wherein m and n each are numbers from 20 to 10,000, in particular 50 to 7,000, especially 100 to 5,000, x is a number between 1 and 5, preferably 3, and y is a number from 5 to 30, $R_{10}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Aqueous compositions according to the present invention can contain organic solvent and also as a solubilzers. Examples of such organic solvents are benzyloxy ethanol, benzyl alcohol, phenoxy ethanol, phenoxy isopropanol, methyl phenoxy ethanol, benzyl glycerol, N-benzyl formide, N-methyl pyrrolidone, N-ethyl pyrrolidone, cinnamyl alcohol, phenethyl alcohol, p-methyl benzyl alcohol, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 0.5% to 10%, preferably 0.5-5% by weight calculated to the total composition.

Aqueous compositions according to the invention preferably contain thickening agents. These are, for example, the various cellulose derivatives such as hydroxyalkyl celluloses, e.g. hydroxyethyl cellulose, hydroxypropyl cellulose, hydroxypropyl methyl cellulose, natural polysaccharides such as xanthan gum; guar gum and the alkoxylation products thereof in amounts from 0.1-5%, preferably 0.1-3% and most preferably 0.1-2% by weight calculated to the total composition and depending on the desired consistency thereof.

Optionally, the composition of this invention can comprise further hair conditioning agents such as silicone oils either volatile or non-volatile, natural and synthetic oils. Among silicone oils those can be added to the colouring composition include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil, isopropyl myristate, palmitate, stearate and isostearate, oleyl oleate, isocetyl stearate, hexyl laurate, dibutyl adipate, dioctyl-adipate, myristyl myristate and oleyl erucate.

Another preferred compound in aqueous compositions of present invention is ceramide type of compounds according to general formula

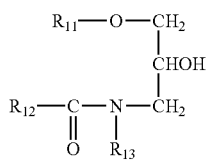

where $R_{11}$ and $R_{12}$ are independent from each other alkyl- or. alkenyl group with 10 to 22 carbon atoms, $R_{13}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide. Concentration of ceramide type of compounds ranges from 0.01 to 2%, preferably 0.01 to 1% by weight calculated to total composition before mixing.

The aqueous compositions of the present invention can comprise of at least one ubiquinone of the formula (I)

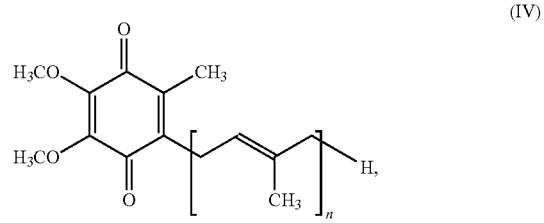

wherein n is a number from 1 to 10. Concentration of ubichinone can vary between 0.001% and 10% by weight, calculated to the total composition before mixing.

Aqueous compositions may as well comprise UV filters of oil soluble, non-ionic, ones and/or as well those of water soluble and mainly of anionic character. Non-limiting examples are Benzophenone-1 Benzophenone-2, Benzophenone-3, Benzophenone-7, Benzophenone-6, Benzophenone-8, octylmethoxy cinnamate, homosalat to those of oil soluble ones and Benzophenone-4, benzophenone-9 to those anionic water soluble ones. It should be noted that the other UV filters of oil and water soluble ones should as well be possible to combine.

In a hair bleaching and/or highlighting and/or colouring process, bleaching and/or highlighting and/or colouring compositions prepared according to any of the processes mentioned above is further applied onto hair and left on the hair for a period of 5 to 30 min and rinsed off with water.

In a further process, the compositions prepared according to any of the process mentioned above, hair is bleached and/or highlighted first by application of a bleaching and/or highlighting composition prepared according to the one of the processes mentioned above and coloured with a colouring composition comprising at least one hair dye preferably a direct dye. In the process mentioned in this paragraph, it is also possible to colour hair with oxidative colouring composition which comprise at least one oxidative dye precursor, optionally at least one coupler and optionally one or more direct dye.

Further object of the present invention is kit for bleaching and/or highlighting and/or colouring hair comprises a powder and/or a granular composition with at least one bleaching and/or highlighting agent, a liquid composition comprising at least one oxidizing agent and a sieve of suitable size.

In addition to the above, kit comprises an additional liquid composition. The additional liquid composition comprises at least one hair conditioning compound and/or at least one alkalizing agent and/or at least one direct dye.

Additionally, kit for bleaching and/or highlighting and/or colouring hair comprises a powder and/or a granular composition with at least one bleaching and/or highlighting agent, a second powder composition comprising at least one direct dye, a liquid composition comprising at least one oxidizing agent and a sieve of suitable size.

The invention is illustrated with the following examples, but not limited to.

EXAMPLE 1

| Bleaching/Highlighting powder composition | |
|---|---|
| Hydroxyethylcellulose | 1.40% by weight |
| Cellulose gum | 3.20 |
| Xanthan gum | 0.30 |
| Tetrasodium EDTA | 2.00 |
| Sodium carbonate | 1.00 |
| Ammonium persulfate | 21.00 |
| Potassium persulfate | 46.60 |
| Sodium metasilicate | 10.20 |
| Corn starch | 1.10 |
| Diatomaceous Earth | 11.10 |
| Polyquaternium-10 | 0.10 |
| Silica* | 1.00 |
| Synthetic fluorphologopite** | 1.00 |

*Aerosil 380
**Synthetic fluorphologopite used is commercially available from Sun Chemical Corporation under the trade name SunShine Glitter White with a particle size distribution in the range of 20 to 95 μm.

The above composition is prepared by combining all powder components together and by mixing until homogeneity in a suitable mixer.

In order to prepare a bleaching composition, the above composition is mixed with an oxidizing lotion of the following formula

| Hydrogen peroxide | 9.00 (% by wt.) |
|---|---|
| Cetyl stearyl alcohol | 1.70 |
| Phosphoric acid | 0.50 |
| Sodium lauryl sulfate | 0.20 |
| Coenzyme Q10 | 0.05 |
| Cetyl PG hydroxyethyl palmitamide | 0.10 |
| Disodium hydrogen phosphate | 0.10 |
| Salicylic acid | 0.10 |
| Water | ad 100.00 | at a weight ratio of 1 part bleaching powder with 2 parts of oxidizing lotion. Powder composition was added to the oxidizing lotion through a sieve with 1 mm opening size. The mixture thus obtained was evaluated to be more homogeneous and creamy than a composition prepared wherein powder composition was directly added to the oxidizing composition.

Hair treated with the above composition was homogeneously bleached and found to be well combable, and having excellent shine. Additionally no side effects were reported.

EXAMPLE 2

Bleaching and colouring in a single process was carried our using the bleaching composition of example 1, dyeing composition according to the composition below and an oxidizing lotion composition of example 1.

| Dyeing composition | |
|---|---|
| | % by weight |
| Cocamide MEA | 4.00 |
| Cetearyl alcohol | 10.00 |
| Tegin P | 1.40 |
| Propylene Glycol | 2.40 |
| Oleic acid | 3.00 |
| Coenzyme Q10 | 0.10 |
| Ammonium chloride | 0.50 |
| Tetrasodium EDTA | 0.20 |
| Sodium lauryl sulfate | 1.50 |
| Polysilicone-9 | 0.20 |
| Pentaphenyl trimethyl trisiloxane | 5.00 |
| Cetyl PG hydroxyethyl palmitamide | 0.10 |
| Basic red 51 | 0.50 |
| Water | to 100 |

In order to prepare bleaching and colouring composition 1 part powder composition was added to the mixture of colouring and oxidizing compositions (1:1 by weight) mixture through a sieve. In a further trial bleaching powder was mixed with colouring composition at a weight ratio of 1:1 and the resulting mixture was further mixed with 1 part of oxidizing lotion.

The mixture thus obtained was evaluated to be more homogeneous and creamy than a composition prepared wherein powder composition was directly added to the colouring and/or oxidizing composition.

The composition thus obtained was applied onto parts of hair (streak) and left 30 min at 40° C. and rinsed off with water and shampooed. Intensive highlighted red streaks were obtained.

Similar results were observed when other cationic, anionic and/or nonionic nitro dyes mentioned in the description are used instead of the cationic dye in the example.

EXAMPLE 3

Bleaching and colouring in a single process was carried out using the bleaching composition of example 1, dyeing composition of example 2 which additionally comprised 0.5% acid red 52 (the amount of water was reduced) and an oxidizing lotion composition of example 1. The mixture was prepared as mentioned in example 2 and was applied onto parts of hair (streak) and left 30 min at 40° C. and rinsed off with water and shampooed. Intensive highlighted red streaks were obtained.

EXAMPLE 4

| Bleaching/Highlighting powder composition | |
|---|---|
| Hydroxyethylcellulose | 1.40% by weight |
| Cellulose gum | 3.20 |
| Xanthan gum | 0.30 |
| Tetrasodium EDTA | 2.00 |
| Sodium carbonate | 1.00 |

-continued

| Bleaching/Highlighting powder composition | |
|---|---|
| Ammonium persulfate | 21.00 |
| Potassium persulfate | 40.60 |
| Sodium metasilicate | 6.20 |
| Corn starch | 1.10 |
| Diatomaceous Earth | 11.10 |
| Polyquaternium-10 | 0.10 |
| Mineral oil | 10.00 |
| Silica* | 1.00 |
| Synthetic fluorphologopite** | 1.00 |

*Aerosil 380
**Synthetic fluorphologopite used is commercially available from Merck with a particle size distribution in the range of 5 to 45 μm.

The above composition was mixed with 1% Basic red 51 and mixed with an oxidizing lotion through a sieve and applied onto parts of hair. Hair was effectively highlighted with shiny red colour.

The invention claimed is:

1. A process for preparing a bleaching and/or highlighting composition consisting of the steps of mixing at least one powder composition being water free bleaching powder and/or granules with a liquid composition, wherein the powder composition is added to a liquid composition by passing through a sieve.

2. The process according to claim 1, wherein the liquid composition comprises at least one hair dye.

3. The process according to claim 1, wherein the liquid composition comprises at least one oxidizing agent.

4. The process according to claim 1, wherein the liquid composition comprises at least one alkalizing agent.

5. The process according to claim 1, wherein the at least one powder composition is mixed with a second powder composition comprising at least one direct dye.

6. The process according to claim 1, wherein the sieve has an opening size of 5 mm or smaller.

* * * * *